United States Patent [19]
Melmed et al.

[11] Patent Number: 5,824,838
[45] Date of Patent: Oct. 20, 1998

[54] TRANSGENIC MOUSE MODEL FOR PITUITARY DISORDERS ASSOCIATED WITH LIF OVEREXPRESSION AND/OR GH UNDEREXPRESSION, AND ITS USE FOR TESTING THERAPEUTIC DRUGS FOR THE CONDITIONS

[75] Inventors: Shlomo Melmed; Sadanori Akita, both of Los Angeles; Carol Readhead, Pasadena, all of Calif.

[73] Assignee: Cedars-Sinai Medical Center, Los Angeles, Calif.

[21] Appl. No.: 647,401

[22] Filed: May 9, 1996

[51] Int. Cl.$^6$ .............................. C12N 5/00; C12N 15/00; C12N 15/09
[52] U.S. Cl. ..................... 800/2; 435/172.3; 435/69.1; 435/69.5; 435/320.1; 435/325; 424/9.21; 536/23.5; 536/23.51
[58] Field of Search ........................ 800/2; 435/69.1, 435/320.1, 172.3, 69.5, 325; 424/9.2, 9.21; 536/23.5, 23.51

[56] References Cited

U.S. PATENT DOCUMENTS

| | | | |
|---|---|---|---|
| 4,736,866 | 4/1988 | Leder et al. | 800/1 |
| 5,175,383 | 12/1992 | Leder et al. | 800/2 |
| 5,175,384 | 12/1992 | Krimpenfort et al. | 800/2 |
| 5,175,385 | 12/1992 | Wagner et al. | 800/2 |
| 5,187,077 | 2/1993 | Gearing et al. | 435/69.1 |
| 5,215,904 | 6/1993 | Gould et al. | 435/172.3 |
| 5,223,610 | 6/1993 | Burton et al. | 536/24 |
| 5,347,075 | 9/1994 | Sorge | 800/2 |
| 5,427,925 | 6/1995 | Gearing et al. | 435/69.5 |
| 5,443,825 | 8/1995 | Gearing et al. | 424/85.1 |

OTHER PUBLICATIONS

Houdebine, Journal of Biotechnology, vol. 34, pp. 269–287, 1994.
Strojek & Wagner, Genetic Engineering: Principles and Methods, vol. 10, pp. 221–246, 1988.
Wall, Theriogenology, vol. 45, pp. 57–68, 1996.
Kappel et al., Current Opinion in Biotechnology, vol. 3, pp. 548–533, 1992.
Hippenmeyer et al., Molecular and Cellular Endocrinology, vol. 107, pp. 155–164, Feb. 1995.
Shen et al., EMBO Journal, vol. 13, pp. 1375–1385, Mar. 15, 1994.
Sittler et al., DNA and Cell Biology, vol. 9, pp. 511–518, Sep. 1990.
Akita et al., Journal of Clinical Investigation, vol. 95, pp. 1288–1298, Mar. 1995.
Liu et al., Molecular and Cellular Biology, vol. 12, pp. 3978–3990, Sep. 1992.
Westphal, FASEB Journal, vol. 3, pp. 117–120, 1989.
Akita, Sadanori, Jonathan Malkin and Shlomo Melmed, "Disrupted Murine Leukemia Inhibitory Factor (LIF) Gene Attenuates Adrenocorticotropic Hormone (ACTH) Secretion," *Endocrinology*, vol. 137, No. 7, pp. 3140–3143.
Akita, Sadanori, et al., "Pituitary–directed Leukemia Inhibitory Factor Transgene Forms Rathke's Cleft Cysts and Impairs Adult Pituitary Function–A Model for Human Pituary Rathke's Cysts," *The Journal of Clinical Investigation*, vol. 99, No. 10, May 1997, pp. 2462–2469.
Bamber, Bruce A. et al., "Leukemia Inhibitory Factor Induces Nuerotransmitter Switching in Transgenic Mice," *Proceedings of the National Academy of Science USA*, vol. 91, pp. 7838–7843, Aug. 1994, Neurobiology.
Shellard, Joan et al., "Role of Leukemia Inhibitory Factor During Mammalian Development," *European Cytokine Network*, vol. 7 No. 4, Dec. 1996, pp. 699–712.
Bamber et al. Aug. 1994, *Proc. Natl. Acad. Sci. USA*, 91:7839–7843.
Barloon et al., Mar./Apr. 1988, *AJNR*, 9:406–407.
Fischer et al., 1990, *J. Neurosurg*, 73:534–540.
Stewart et al., Sep. 1992, *Nature*, 359:76–79.
Yasargil et al., 1990, *J. Neurosurg*, 73:3–11.

Primary Examiner—Jasemine C. Chambers
Assistant Examiner—Jill D. Schmuck
Attorney, Agent, or Firm—Viviana Amzel, Pretty, Schroeder & Poplawski

[57] ABSTRACT

Recombinant transgenic mice expressing leukemia inhibitory factor (LIF) in the pituitary. The transgenic mice of the invention are suitable for use as animal models of pituitary disorders, as well as for identifying compounds which stimulate growth hormone production, for the treatment of physiological disorders associated with growth retardation and pituitary developmental retardation disorders, such as chraneopharyngioma, and pituitary cysts, among others.

35 Claims, 3 Drawing Sheets

TRANSGENIC MOUSE MODEL FOR PITUITARY DISORDERS ASSOCIATED WITH LIF OVEREXPRESSION AND/OR GH UNDEREXPRESSION, AND ITS USE FOR TESTING THERAPEUTIC DRUGS FOR THE CONDITIONS

BACKGROUND OF THE INVENTION

1. Field of the Invention

The present invention relates to transgenic non-human animals and uses therefor. In a particular aspect, the present invention relates to transgenic animals, whose pituitary gland in this mode to overexpress leukemia inhibitory factor (LIF). In another aspect, the present invention relates to animal models for pituitary disorders associated with the regulation of LIF expression.

DESCRIPTION OF THE BACKGROUND

Leukemia Inhibitory Factor (LIF), a pleiotropic cytokine, is a determinant of neuronal, hematopoietic and metabolic development and function. LIF arrests embryonic stem cell differentiation in vitro and small vessel arteriogenesis. In vivo tissue-specific LIF overexpression leads to switching from noradrenergic sympathetic to cholinergic innervation in the pancreas or to altered thymic epithelium and interconversion of thymic and lymph node morphologies. Injection of LIF-producing hematopoietic cells causes cachexia and lethality in mice.

Pituitary LIF and its binding sites are expressed predominantly in human fetal corticotrophs and somatotrophs as early as 14 weeks gestation. LIF potently synergizes with corticotropin releasing hormone (CRH) to enhance prooiomelanocortin (POMC) transcription and adrenocorticotropin (ACTH) secretion in vitro. Conversely, LIF antagonizes CRH-induced pituicyte proliferation by attenuating the cell cycle in its S phase. Furthermore, injection of endotoxic lipopolysacoharide induces both LIF and LIF-receptor expression in the murine hypothalamus and pituitary, concomitantly with ACTH induction. LIF chronically infused into mice bearing a disrupted LIF gene (LIF knockout) stimulates ACTH secretion while attenuating growth hormone (GH) secretion by 39%.

The above described findings imply that LIF acts to regulate both fetal pituitary development as well as adult pituitary functional responses to stress. Therefore, there is a need in the art to determine the effects of pituitary-directed LIF overexpression.

SUMMARY OF THE INVENTION

The present invention relates to transgenic, non-human mammals, whose pituitaries are capable of specifically expressing leukemia inhibitory factor in the pituitary. The transgenic mammals of the invention are useful as animal models of pituitary disorders associated with the regulation of LIF expression. The transgenic mammals of this patient are also useful for identifying compounds which stimulate growth hormone (GH) production, as well as compounds useful for the treatment of physiological disorders associated with craniopharyngioma, and pituitary cysts, and the like.

DETAILED DESCRIPTION OF THE PREFERRED EMBODIMENTS OF THE INVENTION

Figure 1:
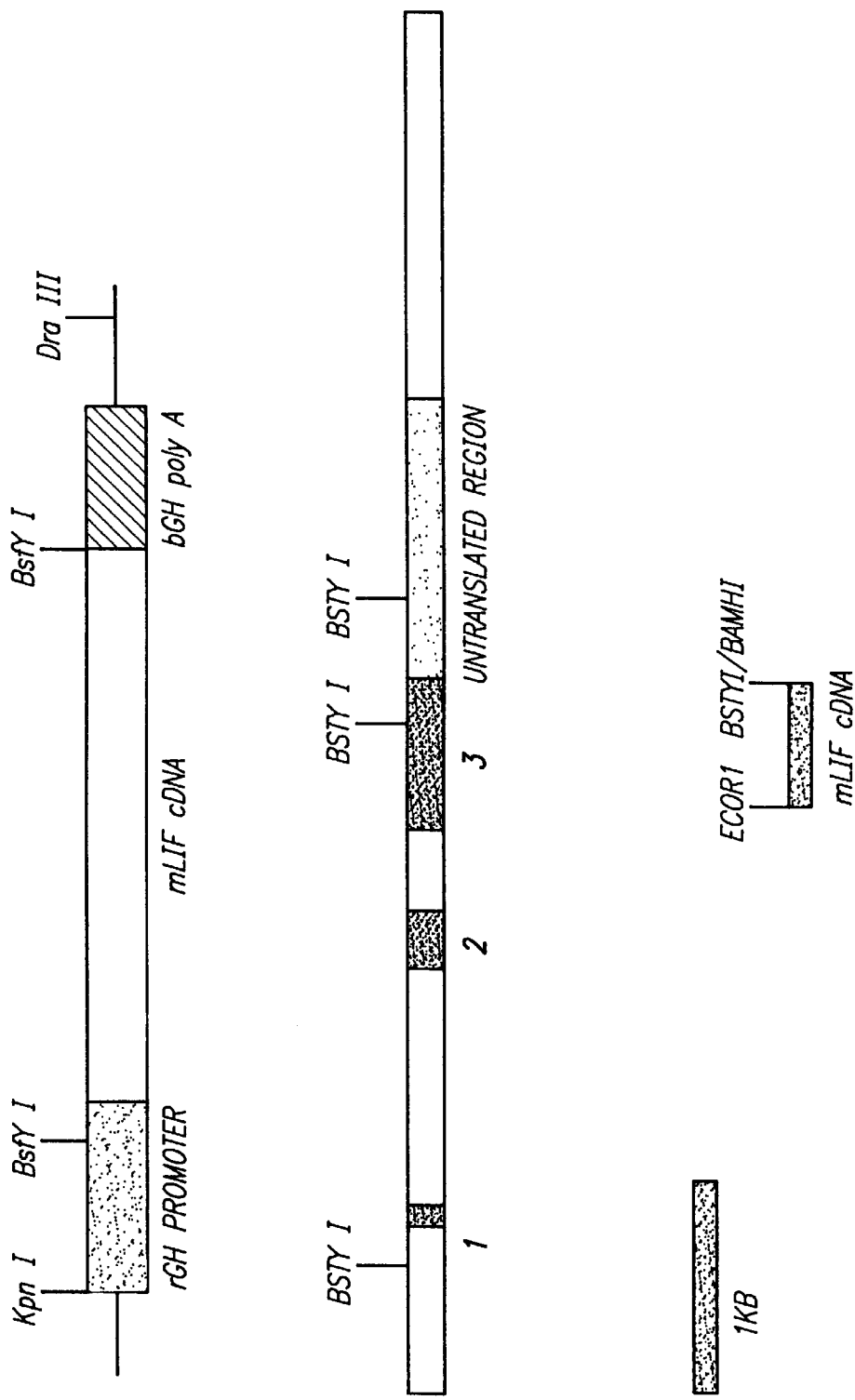
FIG. 1 shows the recombinant murine LIF construct used as the transgene for production of an invention transgenic mammal.
Figure 2A:
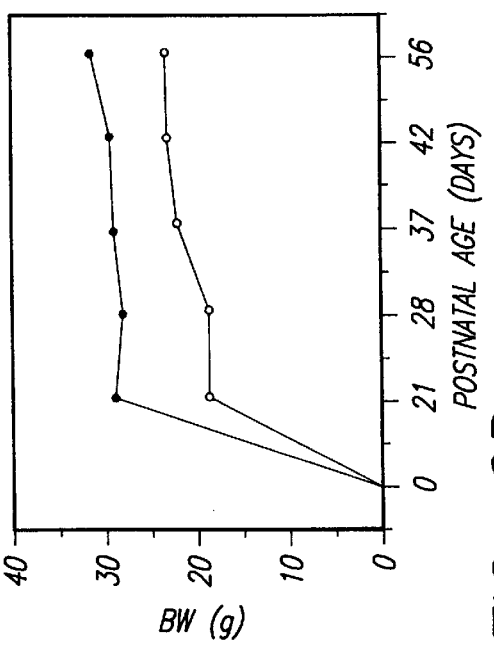
FIGS. 2a, 2b, 2c and 2d show the relative body weights (BW) of 3 founder transgenic mice (F-$O_1$, F-$O_2$, F-$O_3$) and a first generation mouse F-$1_1$, respectively. Wild type (WT) littermates (closed circles) and transgenic mice (open circles) were weighed at 10:00 am on the indicated days. Each data point represents the mean ± range of 2, 1, 3, and 3 WT animals and 1 transgenic mouse in panels a, b, c and d, respectively.
Figure 2B:
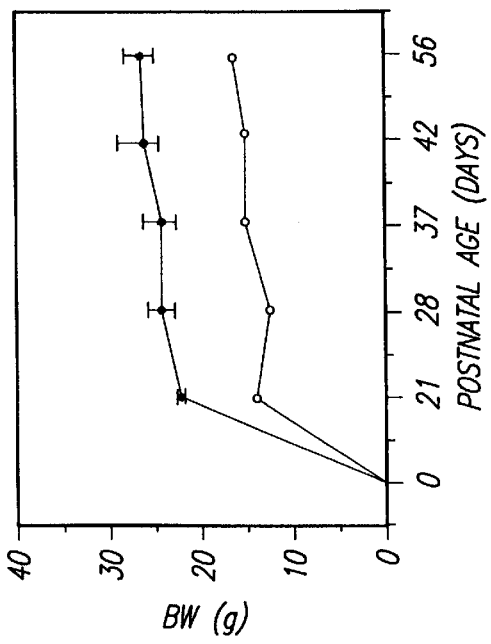
Figure 2C:
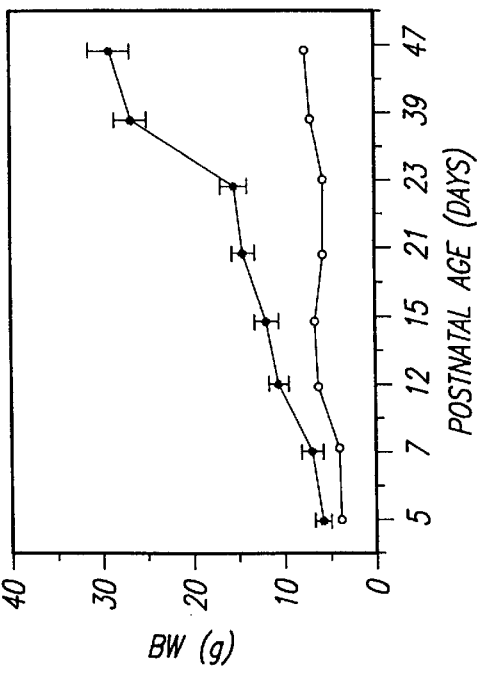
Figure 2D:
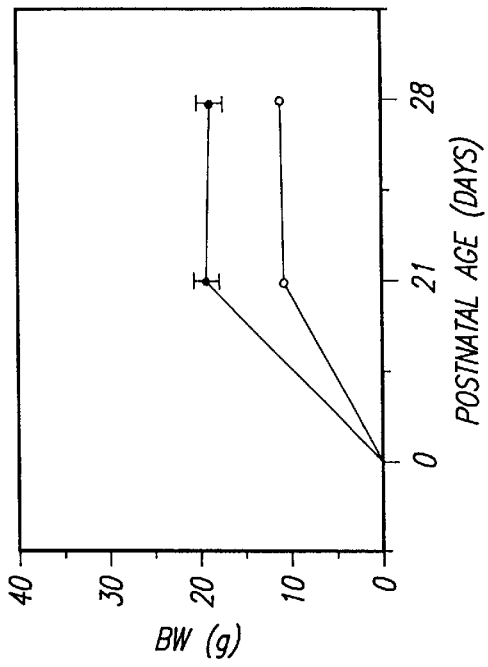

The present invention provides transgenic mammals transfected with a nucleic acid encoding Leukemia Inhibitory Factor (LIF), wherein the transfected nucleic acid converts to the mammal's pituitary the ability to express LIF.

As used herein, "transgenic mammal" refers to a mammal that contains an inheritable recombinant transgene. In accordance with the present invention, any mammalian species can be rendered transgenic by introduction of exogenous nucleic acid encoding LIF. As employed herein, "mammal" embraces all members of the class, e.g., human, rodent, primate, avian, bovine, porcine, ovine, canine, feline, and the like. Preferably, mammals employed in the practice of the present invention are non-human mammals. Presently preferred mammals are rodents, e.g. mice, rats, and the like. Such transgenic mammals may be prepared by well-known methods, such as described in, for example, U.S. Pat. Nos. 4,736,866; 5,175,383; 5,175,384; 5,175,385; 5,347,075; and the like, (each of which are incorporated herein by reference in their entirety).

As used herein, "Leukemia Inhibitory Factor" (LIF), refers to a protein that (1) has the ability to suppress the proliferation of myeloid leukaemia cells such as M1 cells, with associated differentiation of the leukaemic cells; and (2) will compete with a protein having the defined sequence of murine LIF or human LIF for binding to specific cellular receptors on M1 cells or murine or human macrophages (see U.S. Pat. No. 5,427,925). Suitable LIF proteins, and nucleic acids encoding them, which are within the scope, contemplated for use in are the present invention, for example, those described in U.S. Pat. Nos. 5,187,077; 5,427,925; 5,443,825, and the like, each of which is incorporated herein by reference in its entirety. A presently preferred LIF protein and nucleic acid encoding it, is murine LIF (see U.S. Pat. No. 5,187,077).

As employed herein, the phrase "exogenous nucleic acid" refers to nucleic acid sequence which is not native to the host, or which is present in the host in other than its native environment, e.g., as part of a genetically engineered DNA construct. The nucleic acid encoding LIF contemplated for use herein may be obtained from natural sources or may be prepared synthetically. Presently preferred sequences for use herein are those of CDNAs encoding human or murine LIF, with murine LIF being especially preferred.

When an expression construct of the invention contains an endogenous gene encoding a naturally occurring LIF protein, the cDNA for such endogenous gene is generally operatively linked to a promoter different from its native promoter, such that the gene may be overexpressed relative to the naturally occuring expression levels in the corresponding wild type mammal, i.e., the transgenic mammal is capable of producing higher levels of the encoded protein than are naturally produced.

As used herein, an "overexpressed" LIF protein refers to a protein that is produced in higher amounts than are produced endogenously. Overexpression may be achieved, for example, by linking a transgene to an appropriate constitutive promoter, such that the transgene is continually expressed. Alternatively, the transgene may be linked to a strong, inducible promoter so that overexpression may occur on demand.

Suitable levels of LIF overexpression include expression of the transgene about 1.5-fold up to about 1000-fold or more over the naturally occurring level of expression of the endogenous gene. Preferred levels of overexpression are at least about 5-fold, with at least about 10-fold over the naturally occurring level of expression of the endogenous gene being especially preferred.

Transgenes suitable for use in this invention encoding suitable LIF proteins are typically contained in expression constructs. The phrase "expression construct" refers to a DNA molecule that is able to direct the transcription and translation of a structural gene (i.e., cDNA) so that a desired protein is synthesized. The expression generally comprises at least one promoter operatively linked to at least one transgene encoding a desired protein, and a transcription terminator sequence. Thus, the protein-encoding segment is transcribed under regulation of the promoter region, into a transcript capable of providing, upon translation, the desired protein. Appropriate reading frame positioning and orientation of the various segments of the expression construct are within the knowledge of persons of ordinary skill in the art. Further exemplary details are given in the Examples section below.

The "promoter region" refers to the portion of a gene that controls transcription of a DNA, to which it is operatively linked. The promoter region generally includes specific sequences of DNA that are sufficient for RNA polymerase recognition, binding and transcription initiation. The particular promoter selected should be capable of causing sufficient expression to result in the production of an effective amount of LIF protein.

Presently preferred transgenic mammals according to the invention are those which are capable of overproducing LIF specifically in the pituitary. This selective overexpression can be achieved in a variety of ways, e.g., by maintaining LIF under the expression control of a pituitary-specific promoter. Suitable pituitary-specific promoters may be either temporally regulated promoters (e.g., inducible) or they may be constitutive promoters.

Examples of suitable pituitary-specific, temporally regulated inducible promoters include growth hormone (GH) promoters, and the like. A preferred temporally regulated inducible promoter is the rat growth hormone (rGH) promoter. It should be understood that this promoter may not be the optimal one for all embodiments of the present invention. The promoters used in the DNA constructs of the present invention may be modified, if desired, to affect their control characteristics.

Suitable pituitary-specific "constitutive" promoters are those that are active in the pituitary under all environmental conditions and all stages of development or cell differentiation. Pituitary-specific constitutive promoters suitable for use in the practice of the present invention are widely available and are well-known in the art. Exemplary pituitary-specific constitutive promoters include the alpha-subunit promoter, the POMC promoter, the Pit-1 promoter, and the like.

In accordance with another embodiment of the present invention provides nucleic acid construct(s) comprising the above-described expression construct(s). The term "nucleic acid construct," or the abbreviated form "construct," as used herein, and throughout the specification and claims, refers to a recombinant nucleic acid molecule which may include expression constructs, origins of DNA replication, procaryotic and eucaryotic genes from various sources, such as selectable marker genes, repressor genes, as well as any other nucleotide sequences. The construct may be linear or circular in the form of a plasmid vector. A articularly preferred nucleic acid construct is the rGH-mLIF expression construct described in Example 1 and set forth in FIG. 1.

Nucleic acid constructs of the present invention are said to be "operably associated" with one another, such that said transgenes can be translationally expressed to produce the encoded protein under suitable conditions well-known to those of skill in the art.

As used herein the term "plasmid" or "vector" refers to circular, double-stranded DNA loops, which are not bound to the chromosome. Those of skill in the art will recognize that the terms plasmid and vector may be used interchangeably. A plasmid contains DNA capable of causing expression of DNA sequences contained therein, where such sequences are in operational association with other sequences capable of effecting their expression, such as promoter sequences, and the like. The type and number of vectors employed is not critical, so long as the transgenes contained therein are inheritable, e.g., capable of being expressed by each generation of mammal. Suitable vectors for use in expressing the LIF transgenes described herein include: pBluescript SK +/− (Stratagene, La Jolla, Calif.), pcDNA3 (Invitrogen, La Jolla, Calif.), and the like.

The transgenic mammals of the invention, in addition to being capable of overproducing LIF, are typically further characterized as having substantially decreased levels of GH relative to a corresponding wild type mammal. Such reduced levels of GH are typically less than about 50%, preferably 25%, relative to GH levels in a corresponding wild type mammal, with less than about 10% especially preferred. Thus, while GH levels in mammals may vary within wide ranges, invention transgenic mammals into the transgenic mammals of this invention typically display abnormally decreased physiological levels of growth hormone. Accordingly, the transgenic mammals of this invention are useful as animal models for a variety of pituitary disorders and growth hormone deficiency disorders.

For example, the development of pituitary cysts is common in a wide variety of species, including man. In mice, Rathke's pouch is evident at gestational day 8.5; by day 14 its lumen is compressed by the developing adenohypophysis and stalk. By 16 days, all 3 functional components of the pituitary, including the anterior, intermediate and posterior lobes, are evident. Pituitary trophic hormone expression occurs from day 11.5, beginning with the α-subunit, which is restricted to the definitive Rathke's pouch. GH expression is evident only at day 17.5 embryonically, prior to the ultimate obliteration of Rathke's pouch at day 18. Restriction of hormone expression to the specific trophic cell types of the anterior pituitary occurs as the pouch obliterates.

The expression of LIF in the embryonic pituitary of a transgenic mouse according to the present invention resulted in developmental arrest of the murine pituitary. In this transgenic mouse, pituitary cysts could represent failure of the hypophysial cavity to close. Alternatively, cysts may be invaginations from the anterior wall of Rathke's cleft epithelium, which has failed to form differentiated hormone-secreting cells. The cysts appear embryonic in origin since they are lined with primitive epithelial cells immunopositive for cytokeratin and S-100 and immunonegative for trophic hormones. This is in accordance with other studies which have shown LIF to be a potent inhibitor of ectodermal cell differentiation. In a transgenic mouse according to the present invention, expression of LIF in the embryonic pituitary also resulted in dysregulation of the somatotrophs with a 49% decrease in GH secreting cells and undetectable serum GH.

Since the expression of the LIF transgene in the transgenic mice of the invention is controlled by the rat GH promoter, the expression of the LIF transgene would be expected at the same time (embryonic day 17.5) and in the same cell type as endogenous GH. Therefore, dysregulation of the somatotrophs may be due to the overproduction of a transgene product and a generalized disruption of the cellular machinery; or alternatively it could be due to autocrine effects of LIF on the somatotroph cell. Disruption of the cellular machinery by the transgene, however, is unlikely since other transgenes have been expressed using this promoter and endogenous somatotroph function was not disrupted. The low levels of GH mRNA and undetectable circulating GH imply defective GH biosynthesis. In addition, since the 3 separate founder lines described in Example 2 all expressed a similar GH-deficient phenotype, disruption of the endogenous structural GH gene by the transgene is unlikely to have caused GH deficiency. Furthermore, no change was observed in the structure of the GH gene in the transgenic mice when restriction fragments for the GH gene were analyzed.

Since the GH promoter is expected to transactivate gene expression only in the acidophilic precursor stem-cell common to both GH and PRL, it is clear that despite the presence of Pit-1, the pituitary expression of GH in transgenic mice of the present invention is attenuated. Interestingly, the expression of phospho-CREB, which is associated with trans-activation of GH transcription, was lower in the transgenic animal, supporting the conclusion that, in addition to failure of cystic maturation, a direct inhibition of GH transcription is also manifest in the invention transgenic animal model. The degree of growth retardation observed in invention transgenic animals is greater than that seen in other models in which somatotroph lineage was ablated using either thymidine kinase, or diphtheria toxin, or when the GH gene was functionally inactivated using mutated CREB. Interestingly, human fetal corticotrophs express abundant LIF receptors, and in the animal model described herein, pituitary LIF over-expression resulted in corticotroph hyperplasia. The relative abundance of corticotroph cells and induction of POMC mRNA may reflect paracrine stimulation of POMC, as has been shown in vitro, where LIF is a potent inducer of POMC transcription. In vivo, the diffusible alternatively spliced form of LIF mRNA transcript is expressed in the stressed pituitary, lending further credence to a paracrine role for LIF in POMC induction.

The ability to suppress somatotroph lineage development and to induce corticotrophs suggests a novel intrapituitary function for LIF. LIF is therefore a potent regulator of pituitary development after embryonic day 16, when GH expression is initiated. Alternatively, the findings described herein could indicate de-differentiation of committed somatotrophs to more primitive undifferentiated cells in response to LIF.

The expression of the LIF transgene was found to be lethal in utero in at least 12.50 of fetuses screened by embryonic day 18.5. Post-natal transgenic survivors may have had lower intrapituitary LIF expression and these viable mice may reflect a less favorable transgene integration site. Thus, overexpression of pituitary LIF during development both inhibits and stimulates adenohypophysial cells. Pituitary-specific LIF expression also inhibits closure of Rathke's pouch, as well as inhibiting the normal development of somatotrophs and GH production. In contrast, ACTH-producing cells are stimulated in invention transgenic mice. This is in keeping with the function of LIF as an inhibitor of cell differentiation, as well as its ability to markedly change the course of cellular differentiation patterns.

In the pituitary-directed LIF transgenic mice of the invention, the persistence of neuro-ectodermal cysts associated with hypo-expression of GH and PRL provides an animal model for human pituitary cysts or parasellor cysts (which may be associated with growth hormone deficiency). The overexpression of pituitary LIF may also be implicated in the pathogenesis of childhood pituitary cysts, including craniopharyngioma, the most frequent sellar tumor of childhood. These cystic lesions are considered to be derived from cell rests of Rathke's pouch neuro-ectodermal origin and to extend to the diencephalon during fetal development. Children with craniopharyngioma characteristically exhibit short stature, due to GH deficiency, which is the most prevalent hormonal abnormality encountered. The animal model described herein displays an embryological disorder associated with arrested pituitary cysts, thus providing a useful model system for human pituitary cystic disorders and GH deficiency disorders.

Thus, another embodiment of the present invention, provide methods of identifying compounds useful to stimulate production of growth hormone, comprising:

(a) administering test compound(s) to a transgenic mammal of the invention, and (b) detecting an increased level of growth hormone in the serum of the mammal compared to a control transgenic mammal.

Depending on the particular type, the test compounds may be administered to the mammal using a variety of methods well-known to those of skill in the art, such as, for example, orally or by intraperitoneal, intramuscular, intravenous, or subcutaneous injection, and the like. Implant and transdermal modes of administration are also appropriate.

The level of growth hormone in the serum of the mammal can be detected by methods well-known in the art and compared to a control transgenic mammal. Suitable methods include, for example, radioimmunoassays, ELISAs, the methods described in Example 2, and the like. In addition, the relative growth of the mammal can be monitored as an indicator of the level of GH within the mammal.

In accordance with yet another embodiment, the present invention provides methods for identifying compounds useful to treat physiological disorders associated with GH deficiency disorders, such as craniopharyngioma, comprising administering test compounds to a transgenic mammal of the invention, and identifying as useful those compounds that elicit a therapeutic response of pituitary lesion.

As used herein, the phrase "physiological disorders associated with craniopharyngioma" refers to the characteristics exhibited by patients, such as tumor growths and the occurrence of pituitary cysts. See, for example, Yasargil et al., 1990, *J. Neurosurg*, 73:3–11; Barloon et al., *AJNR:*9, March/April 1988, pp. 406–407; and Fischer et al., 1990, *J. Neurosurg*, 73:534–540.

As used herein the phrase "elicit a therapeutic response of pituitary lesion" refers to test compounds that cause involution, shrinkage, or disappearance of the pituitary lesion. Such a response can readily be monitored by those skilled in the art using well-known pathology investigation of autopsy specimens. The sizes of the pituitary lesions for both treated and control transgenic mammals can readily be compared.

In accordance with still another embodiment, the present invention provides methods for identifying compounds useful to treat a physiological disorder associated with pituitary cysts, comprising administering test compounds to a transgenic mammal of the invention, and identifying as useful those compounds that promote a decrease in the size of cystic cavities in the anterior pituitary.

Physiological disorders associated with pituitary cysts (which are exhibited by the invention transgenic animals) include, for example, stunted growth or dwarfism, reproductive failure, short life-span, lung congestion, and the like.

Likewise, such a decrease in the size of cystic cavity can readily be monitored by those skilled in the art using well-known pathology investigation of autopsy specimens. The sizes of the cystic cavities for both treated and control transgenic mammals can readily be compared.

In accordance with another embodiment of the present invention, an isolated cell obtained from an invention transgenic mammal is provided. The transgenic animals of the invention can also be used as a source of cells for cell culture, wherein the transgenic cells are preferably obtained from the pituitary. Cells from the animals may advantageously exhibit desirable properties of both normal and transformed cultured cells; i.e., they will be normal or nearly normal morphologically and physiologically, but can, like cells such as NIH3T3 cells, be cultured for long, and perhaps indefinite, periods of time. Further, where the promoter sequence controlling transcription of the recombinant transgene sequence is temporally regulated and inducible, cell growth rate and other culture characteristics can be controlled by adding or eliminating the inducing factor.

All U.S. patents and all publications mentioned herein are incorporated in their entirety by reference thereto. The invention will now be described in greater detail by reference to the following non-limiting examples.

EXAMPLE

The invention will now be described in greater detail by reference to the following non-limiting examples.

Unless otherwise stated, the present invention was performed using standard procedures, as described, for example in Maniatis et al., *Molecular Cloning: A Laboratory Manual*, Cold Spring Harbor Laboratory Press, Cold Spring Harbor, N.Y., USA (1982); Sambrook et al., *Molecular Cloning: A Laboratory Manual* (2 ed.), Cold Spring Harbor Laboratory Press, Cold Spring Harbor, N.Y., USA (1989); Davis et al., *Basic Methods in Molecular Biology*, Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987)).

Example 1

Preparation of rGH-mLIF Expression Construct

The rGH promoter region (320 bp, KpnI-XhoI) was cloned into Pbluescript SK- (Stratagene) polylinker. A 670 bp EcoRI-BamHI fragment, containing the coding region of the mLIF cDNA was cloned 3' to the promoter region. The rGH-mLIF cDNA hybrid fragment was excised from Bluescript using KpnI and BamHI restriction enzymes and cloned into the pcDNA 3 vector 5' to the bovine GH polyadenylation sites. For microinjection the 1.6 kb construct (FIG. 1) containing the rGH promoter region, the mLIF cDNA and the bGH polyadenylation site was excised from the vector sequences with KpnI and DraIII and purified by gel electrophoresis.

Example 2

Microinjection and Southern Screening

A plasmid containing the GH-LIF fusion gene was constructed by isolation of a 320-bp (KpnI - XhoI) fragment of the rat GH promoter and a 670-bp (EcoRI - BamHI) fragment containing the full length murine LIF cDNA followed by sequential ligations into the polylinker region of pBluescript SK (Stratagene). The KpnI - BamHI sites encompassing the GH-LIF fusion gene were ligated into pcDNA3 vector (Invitrogen), which contains bovine GH polyadenylation sites. The GH-LIF fusion gene for microinjection was prepared by agarose gel electrophoresis of a 1.6 Kb (KpnI - DraIII) fragment and further purified with Elutip (Schleicher & Schuell) . This fragment was microinjected into the pronuclei of fertilized mouse eggs, and the injected eggs transplanted to pseudopregnant foster mothers following standard procedure. All mice were maintained in a pathogen-free environment and provided with food and water ad libitum, histology, immunohistology and in situ hybridization.

Potential founders were screened by Southern blot analysis of tail DNA using a random primer labeled 670-bp fragment containing the full length cDNA of mouse LIF. After microinjection of a rGH-mLIF fusion gene (FIG. 1) into mouse fertilized eggs, progeny of the resultant foster pregnancies were screened for transgene integration. Tail DNA from the pups was digested with BstYI and run on a 1% agarose gel. The DNA transferred to nitrocellulose using a electroblotter. The blot was hybridized with a radiolabeled a 679 bp BamHI-BstYI mLIF cDNA fragment which contained exons 1,2 and part of exon 3. This probe hybridizes to a 3.0 kb BstYI fragment from the endogenous LIF gene and a 0.85 kb BstYI bridging fragment unique to the transgene construct. The endogenous gene served as a copy number control.

Two hundred and fifty pups were screened utilizing a LIF CDNA probe depicted in FIG. 1 and integration of the rGH-mLIF-bGH poly A transgene was confirmed in 3 founder mice by Southern blot analysis. The LIF probe hybridized with a 0.85 kb BstYI bridging fragment unique to the transgene (FIG. 1). From 1 to 3 copies of the transgene were integrated into the founder mice. All 3 founders weighed less than WT littermates (FIGS. 2*a*, 2*b*, 2*c* and 2*d*) . Since one of these transgenic founders (F-O$_3$) died at 4 weeks, two were utilized for breeding. Since no pregnancies were achieved by 22 weeks, their ovaries were transplanted to surrogate recipient B6D2F$_1$ female mice for subsequent establishment of transgenic progeny. Transgene mice had a shorter life-span than WT littermates (up to 5 months), and at autopsy displayed diaphragmatic hypoplasia with chronic lung and liver congestion.

To determine whether undetectable circulating GH was due to structural disruption of the GH gene by the transgene, the integrity of murine GH gene was determined by restriction digestion and Southern analysis utilizing a rat GH cDNA probe. DNA digestion of invention transgenic mouse DNA with ThaI yielded a restriction map of GH which was unaltered compared to wild type (nontransgenic) DNA.

Example 3

Radioimmunoassay for various hormone levels

Raidioimmunoassays were conducted using standard methodology. Mouse GH and PRL RIA kits were provided by Dr. A. F. Parlow, Harbor-UCLA (AFP 10783B, AFP 1077D, respectively). The sensitivity of the GH and PRL RIAs was 0.78 and 0.4 ng/ml, respectively.

Figure 3:
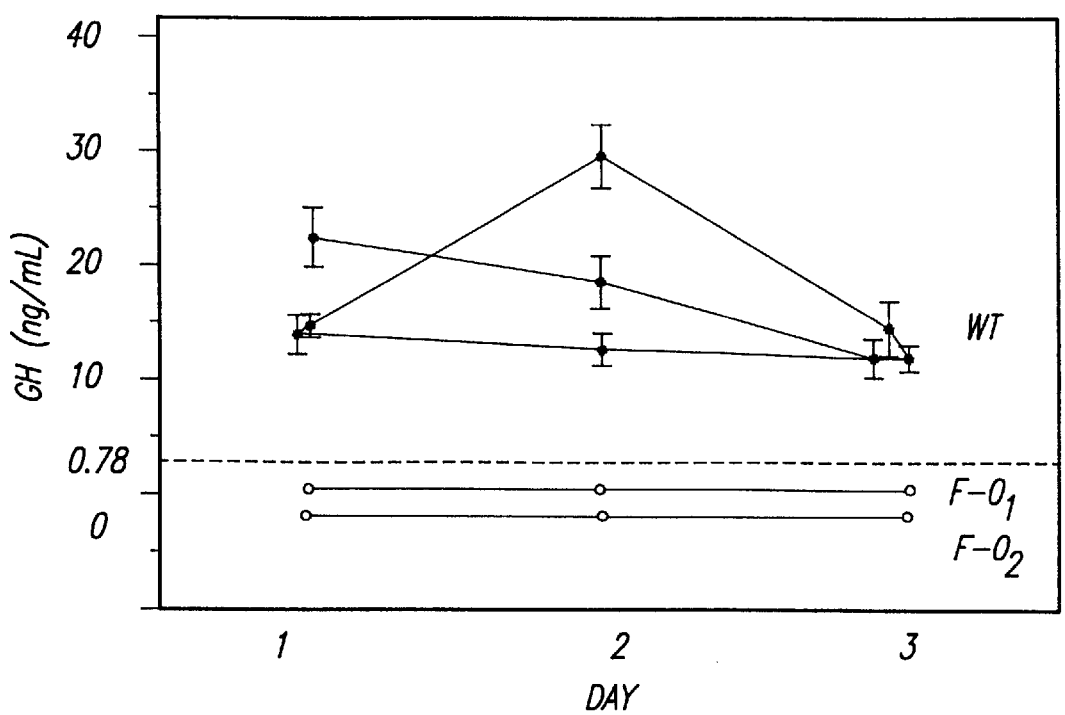
FIG. 3 shows GH levels in WT, F-$O_1$, and F-$O_2$ mice. Retro-orbital blood was obtained from each animal under light anesthesia (methoxyflurane, 10 seconds) at 10:00 am on 3 consecutive days. Each data point represents the mean ± range of duplicate determinations in each animal.

Serum GH levels measured on three consecutive days were undetectable (<0.78 ng/ml) in two transgenic mice (FIG. 3). Serum hormone levels for IGF-I, PRL, and $T_4$ are provided in Table 1. Blood was withdrawn retro-orbitally from WT and transgenic mice at 10:00 am on 3 consecutive days and serum assayed for indicated markers.

TABLE 1

| | Hormone Levels | | |
|---|---|---|---|
| | DAY 1 | DAY 2 | DAY 3 |
| IGF-I (ng/ml) | | | |
| WT | 229 | 271 | 321 |
| | 218 | n.a. | 215 |
| Transgenic (F-0$_1$) | 53 | 94 | 85 |
| PRL (ng/ml) | | | |
| WT | 11 | 14 | n.a. |
| | 10 | 23 | n.a. |
| | 24 | 6 | n.a. |
| Transgenic (F-1$_1$) | 6 | 5 | n.a. |
| T4 (µg/dL) | | | |
| WT | 7.4 | 4.3 | n.a. |
| | 5.9 | 4.3 | n.a. |
| Transgenic (F-1$_1$) | 3.6 | 4.2 | n.a. | n.a = not assayed due to insufficient sample.

From Table 1, it is evident that IGF-I levels were also lower in transgenic animals (53–94 mg/ml vs 215–321 ng/ml, p<0.001), and serum prolactin levels were decreased (5.4±0.43 vs 14.4+2.19, p<0.05). $T_4$ levels were not altered in transgenic animals (Table 1).

Example 4

Immunocytochemistry

The well-known streptavidin-biotin peroxidase complex method was used. The primary antibodies included anti-mouse PRL, anti-rat GH, anti-rat β-FSH, and anti-human ACTH (all kindly donated by National Institute of Diabetes and Digestive and Kidney Diseases, Bethesda, Md., USA).

Pituitary cells immunoreactive for GH, PRL, ACTH and LH were counted with a 40X objective lens within a 0.01 mm ocular grid. The total number of positive cells were expressed as a percentage of the total number of cells within the same area. The counting covered the horizontal section of a pituitary in every case.

The results indicated that LIF immunoreactivity was diffuse in the anterior pituitary lobe and in some cells of the intermediate lobe of both transgenic and WT. However, in transgenic anterior pituitary sections, scattered intense clusters of LIF immunostained cells and several cystic cavities were observed. These were lined by cuboidal, ciliated epithelial cells, focally immunoreactive for cytokeratin and S-100 and immunonegative for pituitary trophic hormones. These cysts are therefore likely to be of primitive neuroectodermal origin. GH and PRL immunostaining was less intense in transgenic mice while ACTH immunopositivity was enhanced.

The results also indicate that somatotroph cell number in transgenic animals was decreased by 47% and GH mRNA expression levels assessed by in situ hybridization was attenuated. In contrast, corticotroph cells were increased by 79% compared to wild type animals.

Example 5

In-Situ Pituitary Hybridizations of Wild Type and Transgenic Mice

Five µm deparaffinized sections were used for the in situ hybridization technique. Pituitaries were fixed in 10% buffered formalin and embedded in paraffin. Five 5 µm sections were stained with hematoxylin-eosin (HE) and periodic acid-Schiff (PAS). GH-, PRL-, and POMC-mRNAs were demonstrated applying oligodeoxynucleotide probes corresponding to amino acids 145–151 of mouse GH, 64–70 of mouse PRL and 99–108 of rat POMC. The probes were labeled by 3'-end method with $^3$S-DATP using a commercially available kit (NEP●100, DuPont Canada, Mississauga, Ontario).

LIF and Pit-1 mRNA were identified using RNA probes. Pit-1 antisense and sense RNA probes were synthesized from a 672 bp cDNA template subcloned in pBluescript KS. After linearization with BamHI and HindIII, transcription was performed using T3 polymerase, and T7 polymerase for antisense probes, respectively. The oligoprobes and RNA probes were purified with NENSORB-TM cartridges (DuPont, Canada). The details of hybridization conditions, autoradiograph and controls were counted with a 100X oil objective over 50–80 adenohypophysial cells. The mean number of silver grains representing nonspecific hybridization was obtained from the number of silver grains on intermediate and posterior lobes, and was subtracted from the mean number of silver grains on anterior lobe cells.

On hematoxylin-eosin stained sections, the normal architecture of pituitary gland was preserved. The posterior and intermediate lobes showed no morphologic changes. The Rathke's cleft separated the anterior lobe from the intermediate lobe. In contrast to control pituitaries, in transgenic mice, the lining epithelium of the anterior wall of Rathke's cleft was ciliated. On some sections, it was noted that the lining epithelium of Rathke's cleft formed deep invaginations into the anterior lobe, and also formed cystic cavities filled with colloid. The anterior lobes of all three transgenic mice contained a decreased number of acidophil cells and a variable number of cystic cavities filled with PAS positive colloid, occasional cell debris, and/or psammoma bodies. The cysts were lined by ciliated, most often cuboidal epithelial cells.

In the anterior lobes of transgenic pituitaries, LIF immunoreactivity showed a diffuse pattern with moderate intensity in the majority of cells and intense LIF immunostaining in scattered cells. In control pituitaries, the LIF immunoreactivity was diffuse. Distinct cells immunostained for LIF were present in intermediate lobes of both transgenic and nontransgenic pituitaries. By in situ hybridization, the signal for LIF mRNA was weak, and diffusely distributed over the anterior and intermediate lobe cells in both transgenic and control pituitaries.

The cysts were evaluated for the presence of epithelial, endothelial, and neuronal immumomarkers, including epithelial membrane antigen, cytokeratin, factor VIII related antigen, glial fibrillary acidic protein, S-100 protein, and anti-human neurofilament protein. Only cytokeratin and S-100 protein were present in substantially all epithelial cells lining the cysts. Some cysts were immunonegative for all markers. In some cysts, 1–2 entrapped hormone-containing cells were found among epithelial cells.

Immunocytochemistry for adenohypophysial hormones revealed the presence of all five types of hormone containing cells. The cell counts demonstrated a 49% decrease of GH immunoreactive cells, and 38% decrease of PRL immunoreactive cells, compared to the adenohypophysial of nontransgenic mice. Many GH immunostained cells were smaller, with an ovoid or angular contour in contrast to control pituitaries in which these cells had a round or polyhedral shape. The quantification of silver grains signaling GH and PRL mRNAs showed a reduction of approximately 50% each. ACTH immunoreactive cells were increased by 80%. No change in the intensity of hybridization signal was observed for POMC mRNA compared to control pituitaries. The percentages of TSH and LH immunoreactive cells were similar to those found in control glands.

Immunocytochemistry for CREB and phosphorylated CREB revealed a marked decrease in the number of nuclei immunoreactive for phosphorylated CREB in anterior lobes of transgenic pituitaries. No change in the intensity of hybridization signal for Pit-1mRNA was found in the adenohypophyses of transgenics in comparison with controls.

Example 6

Fetal Survival Assay

Since the transgene integration rate was low (3.250), it was postulated that the transgene could be lethal in utero. Therefore, after microinjection, timed pregnancies were terminated and fetal viability assessed. The pregnancies were terminated at embryonic day 18.5 and viability of the fetuses was determined. DNA was then extracted from fetal liver and subjected to Southern blot analyses. After termination of embryonic day 18.5, one of 8 fetuses was found demised in utero and its DNA demonstrated transgene integration. Eleven live fetuses observed in 3 separate pregnancies exhibited no transgene integration.

While the invention has been described in detail with reference to certain preferred embodiments thereof, it will be understood that modifications and variations are within the spirit and scope of that which is described and claimed.

That which is claimed is:

1. A transgenic mouse, comprising in its germ and pituitary cells nucleic acid comprising a mouse leukemia inhibitory factor (LIF)-encoding gene regulated by a rat growth hormone pituitary specific promoter operatively linked thereto: wherein with respect to the corresponding wild type mouse,
   the pituitary gland expresses LIF at a level which is at least 1.5 times;
   the circulating levels of growth hormone (GQ) and insulin growth factor-1 (IGF-1) are at least 10% lower; and the mouse's body weight is lower.

2. The transgenic mouse of claim 1, wherein the LIF is expressed at a level up to 1,000-fold over the endogenous LIF level.

3. The transgenic mouse of claim 1, wherein the LIF is expressed at a level at least 5-fold over the endogenous LIF level.

4. The transgenic mouse of claim 3, least 10 to 1,000-fold over the endogenous LIF level.

5. The transgenic mouse of claim 1, having a GH and/or IGF-1 blood level 25% lower than the corresponding wild type mouse.

6. The transgenic mouse of claim 5, having a GH and/or IGF-1 blood level 50% lower than the corresponding wild type mouse.

7. A method of identifying compounds effective for stimulating growth hormone (GH) and/or insulin growth factor 1 (IGF1) production, comprising
   administering a test compound to the transgenic mouse of claim 1;
   determining the mouse's GH and/or IGF1 production prior to, and after, administration of the compound; and
   identifying compounds that increase the mouse's GH and/or IGF1 production after administration of the compound relative to production prior to administration.

8. The method of claim 7, wherein the degree of stimulation of GH and/or IGF1 production is determined by measuring the mouse's relative growth before and after its administration.

9. A method of identifying compounds effective to reduce growth retardation associated with growth hormone (GH) and/or insulin growth factor 1 (IGF1) production deficiency, comprising
   administering a test compound to the transgenic mouse of claim 1;
   determining the mouse's serum level prior to, and after, administration of the compound; and
   identifying compounds that increase the mouse's size after administration of the compound relative to its size prior to administration.

10. A method of identifying compounds effective to reduce pituitary lesion(s), cyst(s), cystic cavity(ies), or craneopharyngioma(s) associated with abnormal pituitary expression of leukocyte inhibitory factor (LIF), comprising administering a test compound to the transgenic mouse of claim 1;
    determining the size of any pituitary lesion(s), cyst(s), cystic cavity(ies), and/or craneopharyngioma(s) present in the mouse prior to, and after, administration of the compound; and
    identifying, compounds that decrease the size of the mouse's pituitary lesion(s), cyst(s), cystic cavity(ies), and/or craneopharyngioma(s).

11. The method of claim 10, wherein the abnormal pituitary expression of LIF is associated with pituitary lesion(s).

12. The method of claim 10, wherein the abnormal pituitary expression of LIF is associated a pituitary cystic disorder.

13. The method of claim 10, wherein the abnormal pituitary expression of LIF is associated with a pituitary cystic cavity.

14. The method of claim 10, wherein abnormal pituitary expression of LIF is associated with a craneopharyngioma (s).

15. A method of identifying compounds potentially effective for treating a pituitary disorder associated with an abnormal pituitary expression of the leukocyte inhibitory factor (LIF), comprising administering a test compound to the transgenic mouse of claim 1;

determining the mouse's LIF pituitary expression prior to, and after, administration of the compound; and identifying compounds that restore the mouse's LIF pituitary expression after administration of the compound to levels found in the corresponding wild-type mouse, wherein the compounds are effective for potentially treating a pituitary disorder.

16. The method of claim 15, wherein the pituitary disorder comprises a pituitary developmental retardation disorder.

17. The method of claim 15, wherein the pituitary disorder comprises a pituitary lesion(s).

18. The method of claim 15, wherein the pituitary disorder comprises a pituitary cystic disorder.

19. The method of claim 15, wherein the pituitary disorder comprises a pituitary cystic cavity.

20. The method of claim 15, wherein the pituitary disorder comprises a craneopharyngioma.

21. An isolated pituitary cell, obtained from the transgenic mouse of claim 1.

22. The cell of claim 21, being an anterior pituitary cell.

23. The cell of claim 22, being a somatic anterior pituitary cell.

24. An isolated pituitary cell, obtained from the transgenic mouse of claim 4.

25. The cell of claim 24, being an anterior pituitary cell.

26. The cell of claim 25, being a somatic anterior pituitary cell.

27. An isolated pituitary cell, obtained from the transgenic mouse of claim 2.

28. The cell of claim 27, being an anterior pituitary cell.

29. The cell of claim 28, being a somatic anterior pituitary cell.

30. An isolated pituitary cell obtained from the transgenic mouse of claim 3.

31. The cell of claim 30, being an anterior pituitary cell.

32. The cell of claim 31, being a somatic anterior pituitary cell.

33. An isolated pituitary cell obtained from the transgenic mouse of claim 5.

34. The cell of claim 33, being an anterior pituitary cell.

35. The cell of claim 34, being a somatic anterior pituitary cell.

* * * * *